US006451615B1

(12) United States Patent
Borg et al.

(10) Patent No.: US 6,451,615 B1
(45) Date of Patent: Sep. 17, 2002

(54) COLORED INDICATOR TO MEASURE THE DISTRIBUTION OF THE HYDROCARBON FAMILIES CONTAINED IN A MIXTURE, THE PROCEDURE FOR OBTAINING IT, AND ITS USES

(75) Inventors: Francoise Borg, Neuilly-sur-Seine; Luc Seyfried, Ecrainville; Dominique Lefebvre, Montivilliers, all of (FR)

(73) Assignee: Total Raffinage Distribution S. A., Puteaux (FR)

( * ) Notice: Subject to any disclaimer, the term of this patent is extended or adjusted under 35 U.S.C. 154(b) by 0 days.

(21) Appl. No.: 09/464,088

(22) Filed: Dec. 16, 1999

(30) Foreign Application Priority Data

Dec. 16, 1998 (FR) .............................. 98 15884

(51) Int. Cl.$^7$ .............................. G01N 21/75
(52) U.S. Cl. .................. 436/166; 436/56; 436/139; 436/164
(58) Field of Search .................. 436/56, 60, 139–142, 436/161, 164, 166, 168; 422/59, 70

(56) References Cited

U.S. PATENT DOCUMENTS 4,210,414 A * 7/1980 Hansen et al. ................ 8/639
4,521,216 A * 6/1985 Armbrust et al. .............. 8/639
5,190,882 A * 3/1993 Schulz et al. ................ 436/139
5,304,493 A * 4/1994 Nowak .......................... 436/56
5,358,873 A * 10/1994 Nowak .......................... 436/56
5,487,770 A   1/1996 Dyllick-Brenzinger et al. ........... 44/328
5,827,332 A   10/1998 Zeidler et al. ................ 44/328

FOREIGN PATENT DOCUMENTS

| JP | 03210472 | 9/1991 | .......... G01N/30/88 |
| WO | 96/00271 | 1/1996 | .......... C10L/1/00 |

OTHER PUBLICATIONS

V. Zrelov et al, "Oxidation–Liquid Chromatography of Fuel Oils", Chem. Technol. Fuel Oils, vol. 16, No. 5–6, 1980 (1980–05), pp. 356–360.
French Search Report.

* cited by examiner

*Primary Examiner*—Jill Warden
*Assistant Examiner*—Yelena Gakh
(74) *Attorney, Agent, or Firm*—Sughrue Mion, PLLC

(57) ABSTRACT

Colored indicator for measuring the distribution of hydrocarbon families contained in a mixture, a procedure for obtaining it and its uses. In the colored indicator, the colorants that are able to be eluted with the family of aromatic hydrocarbons are free of organic compounds having an affinity with oxygenated compounds containing at least 6 carbon atoms.

10 Claims, No Drawings

COLORED INDICATOR TO MEASURE THE DISTRIBUTION OF THE HYDROCARBON FAMILIES CONTAINED IN A MIXTURE, THE PROCEDURE FOR OBTAINING IT, AND ITS USES

This invention concerns a new colored indicator that makes it possible to quantitatively measure the different hydrocarbon families present in a mixture and, in particular, in a gasoline for internal combustion engines with spark ignition, or in a jet propulsion fuel, by the technique using selective retention of these different molecule families on an absorbent carrier. The invention also concerns a procedure for obtaining this new colored indicator and its uses.

STATE OF THE ART

It is known that a fuel intended to supply an internal combustion engine with spark ignition is generally made up of different hydrocarbon families, such as hydrocarbons called "saturated," containing simple bonds between the carbon atoms, such as molecules of the paraffin or naphthene type, as well as hydrocarbons called unsaturated, having benzene cycles, or at least a double bond between the carbon atoms, like molecules with aromatic or olefinic structure.

These different hydrocarbons present in automotive gasoline derive, essentially, from raw petroleum at the beginning of fuel manufacture where numerous chemical transformations take place in the different procedures most often used in a petroleum refinery, for manufacturing of these fuels. The saturated hydrocarbons contained in a fuel make it possible to improve, in a non-limiting manner:

the combustion properties in the cylinders;
the hydrogen/carbon ratio for increasing the calorific power of the fuel;
the stability of the fuel at high temperatures; those such as aromatic hydrocarbons and certain types of olefins promote the increase of:
  the octane index to prevent uncontrolled auto-ignition of the fuel in the cylinders;
  the density, to improve the engine yield while reducing its consumption.

It is also known that, in view of the problems connected with the environment and particularly those posed by emissions from different sources of fossil fuel in the cities, the regulations already in force, and those that are certainly to come, better control of the quantities of these hydrocarbon families introduced into gasoline is required and, in particular, the molecules that are liable to be harmful to air quality and thus to the health of consumers.

Several analytical methods are available to qualitatively and/or quantitatively check the distribution of the molecule families present in a hydrocarbon mixture, for example:

mass spectrometry using the ASTM D2789 method for measurement of aromatic compounds, for example;
gas chromatography and the ASTM D5443 method that make it possible to quantitatively determine paraffins, naphthenes, as well as aromatic molecules;
silica gel chromatography, in application of the ASTM D1319 (or ISO 3837) method for determination of aromatic, olefinic and saturated hydrocarbons.

These different methods make it possible to measure the amount of one or several components present in a hydrocarbon mixture and, in particular, gasoline for internal combustion engines. They differ in their precision, measuring time and also in the complexity of their usage, requiring a mass spectrometer or a simple chromatography column.

Among these methods, the one most used today, the simplest, the least costly and above all the only one currently specified at the international level is silica gel chromatography, conforming to the ASTM D1319 method. This method, called "FIA" which stands for "Fluorescent Indicator Absorption," was standardized in 1954, and makes it possible to detect and measure the quantities of aromatic molecules contained in a gasoline in the range of 5% to 99% by volume, of olefinic between 0.3% and 55% by volume and of all the saturated hydrocarbons between 1% and 95% by volume.

Today, this analytical technique has been maintained in the scope of revising the NF EN228 method, as the reference analysis method in future specifications for internal combustion engine gasoline, in preparation for the year 2000 and relating most especially to the quantitative determination of olefins and aromatic hydrocarbons present in fuels.

The FIA method is based on the principle of liquid phase chromatography, a technique according to which the gasoline or the jet propulsion fuel is eluted with a desorbing alcohol (isopropanol, for example) on a column filled with silica. Separation of the components is shown because of the use of a colored indicator, made up mainly of yellow, blue and red colorings, specific to the hydrocarbon families, which migrate selectively in the column depending on the nature of these hydrocarbons, and of which the coloring can be detected, in particular for the yellow and blue, preferably under an ultraviolet light.

The zone of the column corresponding to saturated hydrocarbons is measured from the front of the elution located at the bottom of the column up to the level of the most intense yellow coloring, since the olefin zone ends at the level of the most intense blue coloring indicating the beginning of the aromatic zone, the latter being limited, above that, by a red ring.

The length of each zone thus identified on the column is directly proportional to the volume of the molecules of the saturated, olefin or aromatic type present in the fuel, the sum of these three zones representing 100% of the hydrocarbons present in the fuel.

One problem posed by this standardized analytical method is that it becomes falsified and leads to erroneous measurements when the fuel being analyzed contains certain oxygen products, as is becoming more and more frequent in fuels that are now on the market.

In fact, it is known, that in order to adjust the fuel octane index, refiners introduce compounds called oxygenated compounds into them, in the form of alcohols, such as methanol or ethanol, in the form of ethers, like methyl-tert-butylether (MTBE), ethyl-tert-butylether (ETBE) or even di-isopropyl ether (DIPE) or tert-amylmethylether (TAME) or mixtures of these oxygenated compounds which prevent the risk of pollution in vehicle exhaust due to organic lead derivatives previously used and for which restrictions against usage are planned in Europe starting in the year 2000, unless there are exceptions which could be agreed upon in certain countries.

The ASTM D1319 method, which was revised twice in 1995, indicates that at the concentrations normally used in commercial gasoline and which usually vary between 5% and 20% by volume, these oxygenated compounds introduced into the gasoline do not interfere with the determination of the hydrocarbon families. These oxygenated compounds are not detected by the FIA method since, with elution with desorbing alcohol, there would be no influence on the distribution of the hydrocarbons in the chromatography column and thus on their measurement.

DETAILED DESCRIPTION OF THE INVENTION

In the course of this work by the FIA method of checking the composition of fuels for internal combustion engines with spark ignition, the Applicant has given evidence, using the tests which will be explained in the following description, that an analysis carried out by the FIA method on a fuel containing oxygenated products, particularly an ether, such as ETBE, leads to considerable deviations in the amounts of hydrocarbons previously obtained in the same fuel without oxygenated products when the ASTM D1319 method is strictly applied.

Thus it appears that the presence of the ETBE and of other oxygenated compounds such as TAME and DIPE, alone or in a mixture with hydrocarbons in the gasoline, is responsible for a systematic error in the measurement of amounts of certain constituents of a gasoline by the FIA method. When the method ASTM D1319 is strictly applied, the rate of aromatic hydrocarbons is overestimated since the amount of saturated hydrocarbons is underestimated.

More precisely, the Applicant has established that the oxygenated products present in the mixtures of hydrocarbons to be analyzed by the FIA method and of which the molecule comprises at least 6 carbon atoms act like aromatic hydrocarbon in the course of elution and explain the deviations recorded by this analysis, in particular when the mixtures contain ETBE.

The colored indicator currently proposed in the method and available commercially is thus not adapted to all types of fuel and notably those that contain, for example, ETBE.

Improvements in these indicators have certainly been proposed, like in DE-A-2 421 793, to increase their readability under the ultraviolet light, but not to make them independent of the composition of the fuel analyzed.

Thus the invention proposes a colored indicator that can be used for determination of the hydrocarbon families present in a mixture by the analysis technique using liquid phase column chromatography, like that given in the ASTM D1319 method, or the equivalent, in which the response is independent of the composition of the sample and, more specifically, of the presence of certain oxygenated compounds that are currently used, alone or in mixtures in gasoline for internal combustion engines.

For this purpose, the first object of the invention is a colored indicator for measuring by liquid phase column chromatography, the amounts of hydrocarbon compounds belonging to the families of saturated, olefin and aromatic hydrocarbons present in the mixture, which also contains oxygenated compounds having at least six carbon atoms, this colored indicator containing substantial quantities of various colorants that are able to be eluted selectively with each of these families by expressing different colors for each of them, and being characterized in that these colorants that are able to be eluted with the aromatic hydrocarbon family are free of organic compounds having an affinity with oxygenated compounds having at least 6 carbon atoms.

According to the invention, the colored indicator may be derived from any type of colored indicator whatsoever for chromatography analysis and, in particular for use of the ASTM D1319 method, for example of the type sold under the name "Fluorescent Indicator" by Universal Oil Products and Merck.

This commercially available colored indicator is made up of a colored gel composed of a mixture of colorant called "Petrol Red AB4" which has been recrystallized and portions of olefinic and aromatic colorants (yellow and blue) purified and deposited on a silica gel.

A red colorant that can also be used in the colored indicator for FIA and well known to the person skilled in the art to be easily eluted by aromatic hydrocarbons is sold under the name "Sudan 3" or "Sudan 4" and belongs to the aromatic azo colorant family and, more generally, to the family of hydroxyaryl compounds that are obtained from Sudan 3 ($C_{22} H_{14} N_4 O$) by a coupling reaction between a derivative of the nitrogen extraction and a coupler of the amine aromatic type.

The Applicant has established that the colorant intended to be eluted by the aromatic hydrocarbons present in fuels, for example, are made up as in the case of Sudan 3, of a mixture of red and brown pigments, the red pigment being eluted by the aromatic compounds and the oxygenated compounds having at least 6 carbon atoms, since the brown pigment is eluted only by aromatic compounds. It is only this brown pigment that is retained by the Applicant and that is included in the new colored indicator to be eluted specifically by the aromatic molecules present in a fuel or a jet propulsion fuel.

Naturally, the colored indicator according to the invention may contain any types of colorants that are able to be eluted with aromatic hydrocarbons if these colorants do not have an affinity for the oxygenated products containing at least 6 carbon atoms and in particular ETBE, TAME, DIPE used alone or in mixtures.

As a result, a second object of the invention is a process for preparation of a colored indicator of the type defined above, starting with a colored indicator of a known type used for the determination by chromatography in liquid phase on a column of the hydrocarbon families continued in a mixture, this procedure being characterized in that, using at least one oxygen compound containing at least 6 carbon atoms, the organic colorants that are able to be eluted by oxygenated compounds containing at least carbon atoms are removed from the known indicator.

More specifically, the known colored indicator obtained by the FIA method is eluted on a chromatography column using a mixture of saturated hydrocarbons, olefins, and aromatics, and the different constituents of this colored indicator are thereby separated and are collected separately. The red colorant thus separated is eluted again on a chromatography column with an oxygenated compound containing at least 6 carbon atoms in order to separate this red colorant into two portions, one red and one brown. The brown portion is collected, and it is closely mixed with the yellow and blue colorants that were previously separated to form the colored indicator according to the invention.

The oxygenated compound with at least 6 carbon atoms used in this procedure is preferably chosen from the group including ETBE, TAME, DIPE or their mixtures.

Another form of extraction of the red colorant from the colored indicator of a known type includes mixing this colored indicator under agitation with oxygenated products having at least 6 carbon atoms, the red colorant thus separated and collected in the organic phase is then eluted in a chromatography column in order to separate it in the way indicated above.

Advantageously, to improve the separation of the red colorant present in the original known colored indicator, an aromatic solvent is used such as toluene, to which the oxygenated compound containing at least 6 carbon atoms is added.

As a result, the colored indicator according to the invention may be prepared using a commercially available red colorant, for example Sudan 3 or Sudan 4, starting from which the brown portion is extracted, for example by elution, this brown portion then being mixed with yellow and blue colorants.

The final object of the present invention is the use of the colored indicator according to the invention to measure the distribution of hydrocarbon families contained in a mixture, by a variation of the FIA method according to the ASTM D1319 method, according to which the reading of the chromatography column is carried out in the usual manner referring to the respective yellow and blue rings for saturated and olefinic hydrocarbons, this application being characterized in that, to detect the end of the aromatic compounds, a brown ring and not a red ring on the chromatography column is taken as a reference, the brown pigment of the colored indicator being eluted specifically by the aromatic hydrocarbons.

The examples below illustrate the invention in a non-limiting manner.

EXAMPLE 1

This example is intended to illustrate the errors appearing in the results of measurement using the FIA method, according to the ASTM D1319 method, of the distribution of hydrocarbon families in a mixture by liquid phase chromatography using a commercial colored indicator when the hydrocarbon mixture contain an oxygenated compound such as ether with at least 6 carbon atoms.

For this purpose, the Applicant has used a commercial gasoline, bearing the reference number SP95, on which analysis has been carried out by strictly applying the ASTM D1319 method, by using the colored indicator sold by Universal Oil Products.

The Applicant then proceeded with the same measurements on the same fuel with a 15% by volume addition of ETBE.

The results obtained are summarized in Table 1 below.

TABLE 1

|  | 1<br>SP95<br>100%<br>FIA Measurements | 2<br>SP 95 = ETBE<br>85% + 15%<br>FIA Measurements |
|---|---|---|
| Aromatic (% v/v) | 28.8 | 36.4 |
| reproducibility (% v) | 3.1 | 3.7 |
| Olefinic (% v/v) | 14.6 | 13.3 |
| reproducibility (% v) | 6.0 | 4.0 |
| Saturated (% v/v) | 56.6 | 50.4 |
| reproducibility (% v) | 5.5 | 4.2 |

In this table, the amounts are expressed, taking a total of 100% aromatic hydrocarbons, olefin hydrocarbons and saturated hydrocarbons as a basis.

Table 1 (column 2) shows that the use of the FIA method, i.e., the measurement of hydrocarbon families contained in a fuel, by the technique of liquid phase chromatography on a column leads to erroneous results if the gasoline analyzed contains ETBE. In fact, significant deviations appear in these results when the measurement is carried out in application of the ASTM D1319 method:

positive and significant deviation (+7.6%) in the measurement of aromatic hydrocarbons.

negative and significant deviation (−6.2%) in the measurement of saturated hydrocarbons.

EXAMPLE 2

In order to better prove the incidence of the presence of oxygenated compounds in the FIA responses, the Applicant has carried out the FIA measurements on two categories of pure oxygenated compounds such as defined in Table 2 and usually encountered in gasoline for internal combustion engines with spark ignition.

TABLE 2

| Oxygenated<br>bases | 1<br>EtOH<br>ethanol | 2<br>TBA<br>tert-butyl alcohol | 3<br>MTBE<br>methyl tert-butyl ether |
|---|---|---|---|
| Global formula | $C_2H_6O$ | $C_4H_{10}O$ | $C_5H_{12}O$ |
| Oxygenated<br>bases | 4<br>ETBE<br>ethyl tert-butyl ether | 5<br>DIPE<br>disopropyl ether | 6<br>MTBE<br>tert-amyl methyl ether |
| Global formula | $C_6H_{14}O$ | $C_6H_{14}O$ | $C_6H_{14}O$ |

These tests yielded the following information:

for the light oxygenated compounds containing, for example 2 to 5 carbon atoms (columns 1, 2 and 3), like ethanol, TBA (tert-butyl alcohol) or MTBE, no FIA response can be attributed to a family of hydrocarbons. The yellow, blue and red colorants specific to the different hydrocarbon families present in the fuel are eluted regularly and cross the column at speeds that are essentially comparable in order to be located at the level of the elution front, at the base of the column thus indicating an absence of FIA response;

for the heavier oxygenated compounds with less than 6 carbon atoms (columns 4, 5 and 6), for example ETBE, DIPE or TAME, the yellow and blue colorants regularly migrate as before to stabilize at the elution front at the bottom of the column since the red colorant progresses more slowly and remains at the bottom of the column in place of the upper limit of the aromatics.

the chromatography column is carried out on the brown rings, since the indicator used does not contain any more red colorant.

The results obtained are summarized in Table 3 below.

TABLE 3

|  | 1 | 2 | 3 | 4 | 5 | 6 |
|---|---|---|---|---|---|---|
|  | Gasoline A | | Gasoline A + 10% MTBE | | Gasoline A + 15% MTBE | |
|  | Colored indicator ASTM D1319 | Colored indicator acc. to the invention | Colored indicator ASTM D1319 | Colored indicator acc. to the invention | Colored indicator ASTM D1319 | Colored indicator acc. to the invention |
| Aromatic (% v/v) | 29.3 | 29.4 | 29.2 | 29.6 | 29. | 29.5 |
| Reproducibility (% v) | 3.2 | | 3.7 | | 3.7 | |
| Olefinic (% v/v) | 9.4 | 10.0 | 9.5 | 9.9 | 9.5 | 10.0 |
| Reproducibility (% v) | 5.1 | | 3.0 | | 3.0 | |
| Saturated (% v/v) | 61.3 | 60.6 | 61.3 | 60.5 | 61.5 | 60.5 |
| Reproducibility (% v) | 5.5 | | 4.2 | | 4.2 | |

|  | 7 | 8 | 9 | 10 |
|---|---|---|---|---|
|  | Gasoline A + 10% ETBE | | Gasoline A + 15% ETBE | |
|  | Colored indicator ASTM D1319 | Colored indicator acc. to the invention | Colored indicator ASTM D1319 | Colored indicator acc. to the invention |
| Aromatic (% v/v) | 34.4 | 29.7 | 38.0 | 29.6 |
| Reproducibility (% v) | 3.7 | | 3.7 | |
| Olefinic (% v/v) | 9.1 | 10.1 | 8.7 | 10.0 |
| Reproducibility (% v) | 3.0 | | 3.0 | |
| Saturated (% v/v) | 56.5 | 60.2 | 53.3 | 60.4 |
| Reproducibility (% v) | 4.2 | | 4.2 | |

According to the application of the ASTM D1319 method, this measurement at the red ring is equivalent to a response corresponding to 100% of the aromatic molecules.

Thus it appears that, in contrast to what the ASTM D1319 method says, the ETBE, the DIPE and the TAME produce a response when the FIA method is used, by virtue of an elution by these oxygenated products with the red colorant (red ring) of the colored indicator provided for by the method, as the aromatic hydrocarbons do. The oxygenated products in which the molecule contains 6 carbon atoms thus behave like aromatic hydrocarbons and explain the deviations recorded by the results of the FIA method when the fuel analyzed contains, for example, ETBE.

EXAMPLE 3

The analytical tests are carried out using the FIA method under the conditions of the ASTM D1319 method, using a gasoline (gasoline A) as a mixture of hydrocarbons for internal combustion engines with spark ignition, alone or with the addition of various quantities of oxygenated compounds, using as a colored indicator:

the colored indicator marketed under the name "Fluorescent Indicator" by Universal Oil Products;

the colored indicator according to the invention, obtained from the preceding by extraction of the red colorant that it contains.

With the colored indicator according to the invention, the reading of the end of the zone of the aromatic compounds on the chromatography column is carried out on the brown rings, since the indicator used does not contain any more red colorant.

These results clearly show that the colored indicator according to the invention makes it possible to carry out reliable measurements using the FIA method, no matter what the nature and quantity of the oxygenated compounds present, in the mixture to be analyzed (columns 2, 4, 6, 8 and 10), which is not the case with the colored indicator provided for by the ASTM D1319 method when the fuel contains an oxygenated compound with at least 6 carbon atoms (columns 7 and 9).

What is claimed is:

1. Colored indicator for measuring by liquid phase colum chromatography the amounts of hydrocarbon compounds selected from saturated, olefinic and aromatic hydrocarbons' families present in a mixture, said mixture including oxygenated compounds, said indicator comprising various colorants that are able to be eluted selectively with each of said families and expressing different colors for each of them and that are provided in quantities sufficient to detect boundaries of colored zones on a chromatography column, comprising colorants that are able to be selectively eluted with the families of aromatic hydrocarbons, said colorants being free of organic compounds having an affinity with oxygenated compounds having at least 6 carbon atoms, wherein the colored indicator is made from a colored indicator for use in the analysis method according to the ASTM D1319 standard, from which the colorants that are able to be eluted with the family of aromatic hydrocarbons and having an affinity with oxygenated compounds containing at least 6 carbon atoms have been eliminated.

2. Colored indicator according to claim 1, wherein the colorants able to be selectively eluted with the family of aromatic hydrocarbons are hydroxyaryl compounds.

3. Colored indicator according to claim 2, wherein the colorants able to be selectively eluted with the family of aromatic hydrocarbons are aromatic azo type compounds.

4. Colored indicator according to claim 1, which is free of red colorant present in the colored indicator provided for use in the analysis method according to the ASTM D1393 standard, but not of brown pigment also present.

5. Procedure for preparation of a colored indicator according to claim 1, comprising providing a colored indicator for use in the analysis method according to the ASTM D1319 standard, said indicator being used for the determination by liquid phase column chromatography of the hydrocarbon families contained in a mixture, and eluting together on a chromatography column at least one oxygenated compound, containing at least 6 carbon atoms, and a red colorant that has affinity to said oxygenated compound, thereby extracting from the colored indicator said red colorant.

6. Procedure according to claim 5, wherein the oxygenated compound containing at least 6 carbon atoms is chosen from the group consisting of ethyl-tert-butylether, tert-amylmethylether, di-isopropyl ether and their mixtures.

7. Procedure according to claim 5, wherein the oxygenated compound with at least 6 carbon atoms is used in a mixture with an aromatic solvent.

8. A method for measuring the distribution of the hydrocarbon families contained in a mixture comprising the steps of:

providing in a chromatography column the colored indicator of claim 1;

eluting the mixture through said chromatography column; and reading said chromatography column by a variation of the FIA method according to the ASTM D1319 standard in which yellow and blue rings refer to saturated and olefinic hydrocarbons, respectively, and, wherein, for detecting the end of aromatic zone, a brown ling, rather than the a red one is taken as a reference on said chromatography column, whereby a brown pigment of said colored indicator is cluted specifically by the aromatic hydrocarbons.

9. The method according to claim 8, in which at least one oxygenated compound of the ether type with at least 6 carbon atoms is also present in the mixture to be analyzed.

10. Procedure according to claim 7, wherein said aromatic solvent is toluene.

* * * * *